(12) United States Patent
Suzuki et al.

(10) Patent No.: US 10,736,826 B2
(45) Date of Patent: Aug. 11, 2020

(54) CREAM-LIKE COMPOSITION

(71) Applicant: AJINOMOTO CO., INC., Tokyo (JP)

(72) Inventors: Takahiro Suzuki, Kawasaki (JP); Kazuhiko Tobita, Tokyo (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 16/239,774

(22) Filed: Jan. 4, 2019

(65) Prior Publication Data

US 2019/0133897 A1 May 9, 2019

Related U.S. Application Data

(63) Continuation of application No. PCT/JP2017/025049, filed on Jul. 7, 2017.

(30) Foreign Application Priority Data

Jul. 8, 2016 (JP) ................. 2016-136241

(51) Int. Cl.
| | |
|---|---|
| *A61K 8/06* | (2006.01) |
| *A61K 8/44* | (2006.01) |
| *A61Q 5/02* | (2006.01) |
| *A61Q 19/10* | (2006.01) |
| *A61Q 1/02* | (2006.01) |
| *A61Q 19/00* | (2006.01) |
| *C11D 3/20* | (2006.01) |
| *A61Q 19/08* | (2006.01) |
| *C11D 1/94* | (2006.01) |
| *C11D 17/00* | (2006.01) |
| *A61Q 5/12* | (2006.01) |
| *A61K 8/34* | (2006.01) |
| *C11D 1/10* | (2006.01) |
| *C11D 1/88* | (2006.01) |

(52) U.S. Cl.
CPC ............ *A61K 8/06* (2013.01); *A61K 8/345* (2013.01); *A61K 8/44* (2013.01); *A61K 8/442* (2013.01); *A61Q 1/02* (2013.01); *A61Q 5/02* (2013.01); *A61Q 5/12* (2013.01); *A61Q 19/00* (2013.01); *A61Q 19/08* (2013.01); *A61Q 19/10* (2013.01); *C11D 1/94* (2013.01); *C11D 3/2041* (2013.01); *C11D 3/2065* (2013.01); *C11D 3/2068* (2013.01); *C11D 17/003* (2013.01); *C11D 1/10* (2013.01); *C11D 1/88* (2013.01)

(58) Field of Classification Search
CPC . A61K 8/06; A61K 8/34; A61K 8/345; A61K 8/44; A61Q 19/10; A61Q 5/02; C11D 17/003; C11D 1/10; C11D 1/88; C11D 1/94; C11D 3/2041; C11D 3/2065; C11D 3/2068

See application file for complete search history.

(56) References Cited

U.S. PATENT DOCUMENTS

2013/0011355 A1   1/2013   Sagawa et al.

FOREIGN PATENT DOCUMENTS

| JP | 62-124200 A | 6/1987 | | |
|---|---|---|---|---|
| JP | 1-294799 A | 11/1989 | | |
| JP | 7-331281 A | 12/1995 | | |
| JP | 8-337519 A | 12/1996 | | |
| JP | H08337519 A | * 12/1996 | ............... | A61K 8/44 |
| JP | 2012-206946 A | 10/2012 | | |
| JP | 2013-517289 A | 5/2013 | | |
| WO | WO2011/088327 | * 7/2011 | ............... | A61K 8/44 |
| WO | WO 2016/104698 A1 | 6/2016 | | |

OTHER PUBLICATIONS

Translation of JPH08337519A, "Matsuzawa" et al., published Dec. 24, 1996. (Year: 1996).*
International Search Report dated Sep. 12, 2017 in PCT/JP2017/025049, 3 pages.
Yokomizo, F., "The Food use of Palm Oil", Food Chemicals, Food Chemicals Newspaper Inc., 2009 Nen The September issue, vol. 25, pp. 24-28.
Fragrance Journal, vol. 2, 1994, pp. 43-48 (with English abstract).

* cited by examiner

*Primary Examiner* — Audrea B Coniglio
(74) *Attorney, Agent, or Firm* — Oblon, McClelland, Maier & Neustadt, L.L.P.

(57) ABSTRACT

Creamy cleansing compositions and creamy compositions which contain (A) at least one component selected from the group consisting of N-acyl acidic amino acid and a salt thereof, and N-acyl neutral amino acid and a salt thereof, (B) at least one polyhydric alcohol, (C) at least one N-mono middle-chain acyl basic amino acid or a salt thereof, and (D) water have good creamy appearance with high grade pearly gloss, are superior in form stability, and superior in the sense of use such as cream elongation, water miscibility, and the like.

17 Claims, No Drawings

CREAM-LIKE COMPOSITION

CROSS REFERENCES TO RELATED APPLICATIONS

This application is a continuation of International Patent Application No. PCT/JP2017/025049, filed on Jul. 7, 2017, and claims priority to Japanese Patent Application No. 2016-136241, filed on Jul. 8, 2016, both of which are incorporated herein by reference in their entireties.

BACKGROUND OF THE INVENTION

Field of the Invention

The present invention relates to creamy compositions which are superior in form stability and sense of use and preferable as a skin composition, a hair composition or a cleansing composition.

Discussion of the Background

It has long been known that N-acyl acidic amino acid salts such as N-acylglutamate and the like and N-acyl neutral amino acid salts such as N-acylglycine salt and the like are useful materials as skin cleansing agents since the foaming pH range thereof is mildly acidic and they are low skin stimulants as compared to those containing, as a main component, fatty acid soap generally used as a facial wash cream.

For example, it has been reported that a creamy cleansing composition such as facial cleansing foam and the like having pearly luster can be obtained by using N-acylglutamate, polyvalent alcohol and water as essential components and setting the mixing ratio of the aforementioned components to fall within a given range (see JP-A-62-124200, which is incorporated herein by reference in its entirety).

However, the creamy cleansing composition reported in JP-A-62-124200 has problems since it produces a small amount of foam, has slyminess, becomes hard at low temperatures and cannot be pushed out easily from the container such as a tube and the like, causes syneresis at high temperatures, cannot maintain good creamy form and the like, and is not entirely a creamy composition superior in the sense of use and morphological stability.

In an attempt to solve the problem of hardening at low temperatures, an embodiment has been reported in which N-long-chain acyl acidic amino acid salt and polyhydric alcohol are further used in combination with an amphoteric surfactant, 2-alkyl-N-carboxymethyl-N-hydroxyethylimidazolinium betaine (see JP-A-1-294799, which is incorporated herein by reference in its entirety).

However, the creamy cleansing composition reported in JP-A-1-294799 still becomes hard when preserved at low temperatures, and a creamy composition having satisfactory low temperature stability has not been obtained.

It has been reported that a creamy cleansing agent that is soft at room temperature and low temperature, superior in foaming, miscible with water, and has a fresh feeling of use can be obtained when a potassium salt is used from among N-long-chain acylglutamates, as compared to the use of triethanolamine salt or sodium salt (see Daisuke Kaneko, Yoshiaki Kawasaki, Properties and Applications of amino acid-based surfactants, FRAGRANCE JOURNAL (2) 43-48 (1994), which is incorporated herein by reference in its entirety).

However, such creamy cleansing agent has problems in that the surface of the composition develops a state of liquid seeping out (syneresis), the cleansing agent becomes too soft and drips down at a high temperature, and further, crystal grain is developed when the agent is exposed to high temperature conditions once and thereafter to a temperature decrease. Thus, the creamy composition cannot be said to be superior in preservation stability and form stability.

Therefore, a creamy cleansing composition, and further, a creamy composition for skin, hair or the like, each containing an N-acyl acidic amino acid salt or an N-acyl neutral amino acid salt as a main component, which compositions suppress an increase in the hardness at a low temperature, simultaneously show good form stability and pearly gloss, and are superior in sense of use, have been desired.

SUMMARY OF THE INVENTION

Accordingly, it is one object of the present invention to provide novel creamy cleansing compositions and creamy compositions for skin, hair or the like, each containing N-acyl acidic amino acid or a salt thereof or N-acyl neutral amino acid or a salt thereof as a main component and having good creamy appearance with high grade pearly gloss, superior in form stability, and superior in the sense of use such as cream elongation, water miscibility and the like.

This and other objects, which will become apparent during the following detailed description, have been achieved by the inventors' discovery that, in a creamy composition containing N-acyl acidic amino acid or a salt thereof or N-acyl neutral amino acid or a salt thereof as a main component, the appearance, form stability and sense of use of the composition can be improved by adding a creamy cleansing composition containing N-mono middle-chain acyl basic amino acid such as $N^\varepsilon$-octanoyl lysine and the like or a salt thereof.

Therefore, the present invention provides the following:

(1) A creamy composition comprising
(A) at least one kind selected from the group consisting of N-acyl acidic amino acid and a salt thereof, and N-acyl neutral amino acid and a salt thereof,
(B) polyhydric alcohol,
(C) N-mono middle-chain acyl basic amino acid or a salt thereof, and
(D) water.

(2) A creamy cleansing composition comprising
(A) at least one kind selected from the group consisting of N-acyl acidic amino acid and a salt thereof, and N-acyl neutral amino acid and a salt thereof,
(B) polyhydric alcohol,
(C) N-mono middle-chain acyl basic amino acid or a salt thereof, and
(D) water.

(3) The composition of (1) or (2), wherein (A) N-acyl acidic amino acid and a salt thereof are N-acylglutamic acid and a salt thereof.

(4) The composition of any of (1) to (3), wherein (A) N-acyl neutral amino acid and a salt thereof are N-acylglycine and a salt thereof.

(5) The composition of any of (1) to (4), wherein (B) polyhydric alcohol is at least one kind selected from the group consisting of alkanediol having 3 to 4 carbon atoms, glycerol and dipropylene glycol.

(6) The composition of any of (1) to (5), wherein (C) N-mono middle-chain acyl basic amino acid or a salt thereof is $N^\varepsilon$-octanoyl lysine or a salt thereof.

(7) The composition of any of (1) to (6), further comprising (E) N-mono long-chain acyl basic amino acid or a salt thereof.

(8) The composition of (7), wherein (E) N-mono long-chain acyl basic amino acid or a salt thereof is N-lauroyllysine or a salt thereof.

(9) A cleansing agent comprising the composition of any of (2) to (8).

(10) A creamy composition comprising
(A) at least one kind selected from the group consisting of N-acyl acidic amino acid and a salt thereof, and N-acyl neutral amino acid and a salt thereof,
(B) polyhydric alcohol,
(C) N-mono middle-chain acyl basic amino acid, wherein the middle-chain acyl is a saturated or unsaturated aliphatic acyl group having 6 to 10 carbon atoms, excluding N-mono middle-chain acyl arginine, or a salt thereof, and
(D) water.

(11) A creamy cleansing composition comprising
(A) at least one kind selected from the group consisting of N-acyl acidic amino acid and a salt thereof, and N-acyl neutral amino acid and a salt thereof,
(B) polyhydric alcohol,
(C) N-mono middle-chain acyl basic amino acid, wherein the middle-chain acyl is a saturated or unsaturated aliphatic acyl group having 6 to 10 carbon atoms, excluding N-mono middle-chain acyl arginine, or a salt thereof, and
(D) water.

(12) The composition according to (10) or (11), wherein (A) N-acyl acidic amino acid and a salt thereof is N-acylglutamic acid and a salt thereof.

(13) The composition according to any one of (10) to (12), wherein (A) N-acyl neutral amino acid and a salt thereof are N-acylglycine and a salt thereof.

(14) The composition according to any one of (10) to (13), wherein (B) polyhydric alcohol is at least one kind selected from the group consisting of alkanediol having 3 to 4 carbon atoms, glycerol and dipropylene glycol.

(15) The composition according to any one of (10) to (14), wherein (C) N-mono middle-chain acyl basic amino acid or a salt thereof is $N^\varepsilon$-octanoyl lysine or a salt thereof.

(16) The composition according to any one of (10) to (15), further comprising (E) N-mono long-chain acyl basic amino acid, wherein the long-chain acyl is a saturated or unsaturated aliphatic acyl group having 12 to 22 carbon atoms, excluding N-mono long-chain acyl arginine, or a salt thereof.

(17) The composition according to (16), wherein (E) N-mono long-chain acyl basic amino acid or a salt thereof is N-lauroyllysine or a salt thereof.

(18) A cleansing agent comprising the composition according to any one of (11) to (17).

Effect of the Invention

The creamy composition and creamy cleansing composition of the present invention have a good creamy appearance with high grade pearly gloss, show good temperature stability and are superior in form stability, and also superior in the sense of use such as elongation, water miscibility and the like.

The creamy composition of the present invention is useful as a skin composition or a hair composition and favorably used for creamy skin cosmetics, sunscreen cosmetics, body cosmetics, make-up cosmetics, hair cosmetics and the like.

In addition, the creamy cleansing composition of the present invention is favorably used for skin cleanser, hair cleanser, body cleanser and the like.

DETAILED DESCRIPTION OF THE PREFERRED EMBODIMENTS

The creamy composition and creamy cleansing composition of the present invention (hereinafter both are sometimes to be also referred to as "the composition of the present invention") contains (A) at least one kind selected from the group consisting of N-acyl acidic amino acid and a salt thereof, and N-acyl neutral amino acid and a salt thereof, (B) polyhydric alcohol, (C) N-mono middle-chain acyl basic amino acid or a salt thereof, and (D) water.

In the present specification, the term "creamy" refers to a state having a soft, smooth and glossy appearance with strong whiteness, which can be filled in a container such as a tube, a jar and the like and easily extruded or easily scooped up with finger tips, and is free of a dripping phenomenon or remarkable stringing phenomenon.

The N-acyl acidic amino acid contained as component (A) in the composition of the present invention is an N-acylation derivative of acidic amino acid. The acidic amino acid of the derivative is, for example, an amino acid showing acidity such as glutamic acid, aspartic acid, 2-aminoadipic acid, cysteine acid, homocysteine acid and the like, may be any of L-form, D-form, DL-form, L-form and DL-form are preferably used and L-form is more preferably used.

For the object of the present invention, N-acylglutamic acid and N-acylaspartic acid are preferably used as N-acyl acidic amino acid salt, and N-acylglutamic acid is more preferably used.

The N-acyl neutral amino acid contained as component (A) in the composition of the present invention is an N-acylation derivative of a neutral amino acid. Examples of the neutral amino acid in the derivative include glycine, alanine, β-alanine, N-methyl-β-alanine, sarcosine, threonine and the like. When an optical isomer is present, it may be any of L-form, D-form and DL-form, L-form and DL-form are preferably used, and L-form is more preferably used.

For the object of the present invention, N-acylglycine and N-acylalanine are preferably used as N-acyl neutral amino acid, and N-acylglycine is more preferably used.

Examples of the acyl group in the above-mentioned N-acyl acidic amino acid and N-acyl neutral amino acid include straight chain or branched chain saturated acyl group having about 6 to 22 carbon atoms such as hexanoyl (caproyl), octanoyl (capryloyl), 6-methylheptanoyl (isooctanoyl), 2-ethylhexanoyl, decanoyl (caprinoyl), dodecanoyl (lauroyl), tetradecanoyl (myristoyl), 12-methyltridecanoyl (isomyristoyl), hexadecanoyl (palmitoyl), 14-methylpentadecanoyl (isopalmitoyl), octadecanoyl (stearoyl), 16-methylheptadecanoyl (isostearoyl), eicosanoyl (arachidoyl), docosanoyl (behenoyl) and the like, and straight chain or branched chain unsaturated acyl group having about 6 to 22 carbon atoms such as hexenoyl, octhenoyl, 6-methylhepthenoyl (isoocthenoyl), decenoyl, dodecenoyl, tetradecenoyl, 9-hexadecenoyl (palmitoleoyl), 9-octadecenoyl (oleoyl), docosenoyl and the like. It may be a mixture of saturated or unsaturated acyl group having about 8 to 18 carbon atoms such as coconut oil fatty acid acyl (cocoyl), palm oil fatty acid acyl and the like.

For the object of the present invention, a straight chain or branched chain saturated acyl group having about 8 to 18 carbon atoms is preferable, a straight chain saturated acyl group having about 12 to 18 carbon atoms is more preferable, and a straight chain saturated acyl group having 12 to 14 carbon atoms is particularly preferable. A particularly preferable acyl group also includes coconut oil fatty acid acyl (cocoyl).

As a salt of the above-mentioned N-acyl acidic amino acid and N-acyl neutral amino acid, alkali metal salt such as sodium salt, potassium salt and the like; alkaline earth metal salt such as magnesium salt, calcium salt and the like; ammonium salt; organic amine salt such as diethanolamine salt, triethanolamine salt and the like; basic amino acid salt such as lysine salt, arginine salt and the like, and the like can be mentioned and, from the aspects of easy availability and handling property, sodium salt, potassium salt or triethanolamine salt is preferable, and sodium salt or potassium salt is particularly preferable.

In the present invention, N-acyl acidic amino acid and a salt thereof are not particularly limited, and those conventionally used for cosmetic compositions can be used. Examples thereof include N-lauroylaspartic acid, N-lauroylaspartic acid sodium salt, N-lauroylaspartic acid disodium salt, N-lauroylaspartic acid potassium salt, N-lauroylaspartic acid triethanolamine, N-myristoylaspartic acid, N-myristoylaspartic acid sodium salt, N-myristoylaspartic acid disodium salt, N-myristoylaspartic acid potassium salt, N-myristoylaspartic acid triethanolamine, N-cocoylaspartic acid, N-cocoylaspartic acid sodium salt, N-cocoylaspartic acid disodium salt, N-cocoylaspartic acid potassium salt, N-cocoylaspartic acid triethanolamine, N-lauroylglutamic acid, N-lauroy L-glutamic acid sodium salt, N-lauroylglutamic acid disodium salt, N-lauroylglutamic acid potassium salt, N-lauroylglutamic acid triethanolamine, N-myristoylglutamic acid, N-myristoyglutamic acid sodium salt, N-myristoylglutamic acid disodium salt, N-myristoylglutamatic acid potassium salt, N-myristoylglutamic acid triethanolamine, N-cocoylglutamic acid, N-cocoylglutamic acid sodium salt, N-cocoylglutamic acid disodium salt, N-cocoylglutamic acid potassium salt, N-cocoylglutamic acid triethanolamine and the like. Among these, N-lauroyglutamic acid sodium salt, N-lauroylglutamic acid disodium salt, N-lauroylglutamic acid potassium salt, N-myristoyglutamic acid sodium salt, N-myristoylglutamic acid disodium salt, N-myristoylglutamic acid potassium salt, N-cocoylglutamic acid sodium salt, N-cocoylglutamic acid disodium salt, N-cocoylglutamic acid potassium salt and the like are more preferably used.

Also in the present invention, N-acyl neutral amino acid and a salt thereof are not particularly limited, and those conventionally used for cosmetic compositions can be used. Examples thereof include N-lauroylglycine, N—N-lauroylglycine sodium salt, N-lauroylglycine potassium salt, N-lauroylglycine triethanolamine, N-myristoylglycine, N-myristoylglycine sodium salt, N-myristoylglycine potassium salt, N-myristoylglycine triethanolamine, N-cocoylglycine, N-cocoylglycine sodium salt, N-cocoylglycine potassium salt, N-cocoylglycine triethanolamine, N-lauroylalanine, N-lauroylalanine sodium salt, N-lauroylalanine potassium salt, N-lauroylalanine triethanolamine, N-myristoylalanine, N-myristoylalanine sodium salt, N-myristoylalanine potassium salt, N-myristoylalanine triethanolamine, N-cocoylalanine, N-cocoylalanine sodium salt, N-cocoylalanine potassium salt, N-cocoylalanine triethanolamine, N-lauroyl-N-methyl-β-alanine, N-lauroyl-N-methyl-β-alanine sodium salt, N-lauroyl-N-methyl-β-alanine potassium salt, N-lauroyl-N-methyl-β-alanine triethanolamine, N-myristoyl-N-methyl-β-alanine, N-myristoyl-N-methyl-β-alanine sodium salt, N-myristoyl-N-methyl-β-alanine potassium salt, N-myristoyl-N-methyl-β-alanine triethanolamine, N-cocoyl-N-methyl-β-alanine, N-cocoyl-N-methyl-β-alanine sodium salt, N-cocoyl-N-methyl-β-alanine potassium salt, N-cocoyl-N-methyl-β-alanine triethanolamine, N-lauroylsarcosine, N-lauroylsarcosine sodium salt, N-lauroylsarcosine potassium salt, N-lauroylsarcosine triethanolamine, N-myristoylsarcosine, N-myristoylsarcosine sodium salt, N-myristoylsarcosine potassium salt, N-myristoylsarcosine triethanolamine, N-cocoylsarcosine, N-cocoylsarcosine sodium salt, N-cocoylsarcosine potassium salt, N-cocoylsarcosine triethanolamine and the like. Among these, N-lauroylglycine sodium salt, N-lauroylglycine potassium salt, N-myristoylglycine sodium salt, N-myristoylglycine potassium salt, N-cocoylglycine sodium salt, N-cocoylglycine potassium salt and the like are more preferably used.

In the present invention, one kind of the above-mentioned N-acyl acidic amino acid and a salt thereof, and N-acyl neutral amino acid and a salt thereof may be selected and used alone, or two or more kinds thereof may be selected and used in combination.

In the present invention, N-acyl acidic amino acid and a salt thereof and N-acyl neutral amino acid and a salt thereof may be synthesized by a method known per se, for example, by a Schotten-Baumann reaction of acidic amino acid, and fatty acid halide converted from fatty acid by a conventional method under alkali conditions, and the like, and commercially available products provided by Ajinomoto Co., Inc. and the like are conveniently used.

The composition of the present invention contains (A) at least one kind selected from the group consisting of N-acyl acidic amino acid and a salt thereof, and N-acyl neutral amino acid and a salt thereof in a proportion of generally 20 wt % to 50 wt %, preferably 25 wt % to 45 wt %, more preferably 30 wt % to 40 wt %, relative to the total amount of the composition.

Examples of the polyhydric alcohol contained in the composition of the present invention as component (B) include divalent alcohols such as straight chain or branched chain alkanediol having about 3-9 carbon atoms (e.g., 1,2-propanediol (propylene glycol), 1,3-propanediol, 1,2-butanediol, 1,3-butanediol (1,3-butylene glycol), 2,3-butanediol, 2-methyl-1,2-propanediol, 2-methyl-1,3-propanediol, 1,2-pentanediol (pentyleneglycol), 2-methyl-2,4-pentanediol (hexyleneglycol), 2-ethyl-2-butyl-1,3-propanediol and the like), dihydroxyalkylether such as dipropylene glycol and the like, polyethylene glycol having an average molecular weight of about 200-20,000 and the like; glycerol such as glycerol, diglycerol and the like and condensates thereof; sugar alcohol such as erythritol, pentaerythritol, arabinitol, sorbitol, mannitol, maltitol and the like, and the like. One kind of these may be selected and used alone, or two or more kinds thereof may be selected and used in combination.

In the present invention, the above-mentioned polyvalent alcohol may be synthesized by a method known per se, and commercially available products provided by each company are conveniently used.

For the object of the present invention, as (B) polyvalent alcohol, divalent alcohol such as alkanediol having 3 to 4 carbon atoms (e.g., 1,2-propanediol (propylene glycol), 1,3-propanediol, 1,2-butanediol, 1,3-butanediol (1,3-butylene glycol), 2,3-butanediol, 2-methyl-1,2-propanediol, 2-methyl-1,3-propanediol and the like), dipropylene glycol, polyethylene glycol 400 and the like; glycerol; hexitol such as sorbitol and the like, and the like are preferably used, the aforementioned alkanediol having 3 to 4 carbon atoms, dipropylene glycol, glycerol and the like are more preferably used, and 1,2-propanediol (propylene glycol), 1,3-propanediol, 1,3-butanediol (1,3-butylene glycol), dipropylene glycol, glycerol and the like are further preferably used.

The composition of the present invention contains (B) polyvalent alcohol in a proportion of generally 15 wt % to 55 wt %, preferably 20 wt % to 50 wt %, more preferably 25 wt % to 45 wt %, relative to the total amount of the composition.

The N-mono middle-chain acyl basic amino acid contained as component (C) in the composition of the present invention is a basic amino acid having one middle-chain acyl group bonded to the α-position amino group or ω-position amino group.

Examples of the basic amino acid constituting the N-mono middle-chain acyl basic amino acid include lysine, ornithine, 2,4-diaminobutyric acid, arginine, histidine and the like.

For the object of the present invention, lysine is preferably used as the above-mentioned basic amino acid.

As the basic amino acid, any of L-form, DL-form and D-form may be used, L-form and DL-form are preferably used and L-form is more preferably used.

The middle-chain acyl group to be bonded to the basic amino acid is a saturated or unsaturated aliphatic acyl group having 6 to 10 carbon atoms, and may be linear or may have a branched chain. Specifically, hexanoyl (caproyl), heptanoyl, octanoyl (capryloyl), octhenoyl, 2-ethylhexanoyl, nonanoyl, decanoyl (caprinoyl), decenoyl and the like can be mentioned.

For the object of the present invention, acyl group having 8 carbon atoms is preferable, and octanoyl (capryloyl) is more preferable.

The binding site of the above-mentioned middle-chain acyl group to the basic amino acid is the α-position amino group or ω-position amino group. For arginine and histidine, it is α-position amino group.

Therefore, examples of the N-mono middle-chain acyl basic amino acid contained as component (C) in the composition of the present invention include $N^\varepsilon$-hexayllysine, $N^\varepsilon$-octanoyllysine, $N^\varepsilon$-2-ethylhexanoyllysine, $N^\varepsilon$-decanoyllysine, $N^\alpha$-hexanoyllysine, $N^\alpha$-octanoyllysine, $N^\alpha$-2-ethylhexanoyllysine, $N^\alpha$-decanoyllysine, $N^\delta$-hexanoylornithine, $N^\delta$-octanoylornithine, $N^\delta$-decanoylornithine, $N^\alpha$-hexanoylornithine, $N^\alpha$-octanoylornithine, $N^\alpha$-decanoylornithine, $N^\gamma$-hexanoyl-2,4-diaminobutyric acid, $N^\gamma$-octanoyl-2,4-diaminobutyric acid, $N^\alpha$-hexanoyl-2,4-diaminobutyric acid, $N^\alpha$-octanoyl-2,4-diaminobutyric acid, $N^\alpha$-hexanoylarginine, $N^\alpha$-octanoylarginine, $N^\alpha$-hexanoylhistidine, $N^\alpha$-octanoylhistidine and the like.

The N-mono middle-chain acyl basic amino acid contained as component (C) in the composition of the present invention may be a free form or a salt form.

Examples of the salt of N-mono middle-chain acyl basic amino acid include alkali metal salts such as sodium salt, potassium salt and the like; alkaline earth metal salts such as magnesium salt, calcium salt and the like; inorganic acid salts such as hydrochloride, nitrate, sulfate, carbonate and the like; organic acid salts such as acetate, lactate, citrate and the like; amino acid salts such as glutamate, aspartate and the like, and the like. From the aspects of easy availability and handleability, sodium salt, potassium salt, acetate and the like are preferable.

For the object of the present invention, a free form is most preferably used.

One kind of the above-mentioned N-mono middle-chain acyl basic amino acid or a salt thereof may be selected and used alone, or two or more kinds thereof may be selected and used in combination From the aspects of yield and operability during production in the present invention, $N^\varepsilon$-octanoyl lysine, particularly $N^\varepsilon$-octanoyl-L-lysine, is preferably used.

In another embodiment, (C) the N-mono middle-chain acyl basic amino acid is one in which the middle-chain acyl is a saturated or unsaturated aliphatic acyl group having 6 to 10 carbon atoms, excluding N-mono middle-chain acyl arginine or a salt thereof.

The above-mentioned (C) N-mono middle-chain acyl basic amino acid or a salt thereof can be used by preparing by a known production method such as a dehydration condensation reaction of fatty acid and basic amino acid.

The composition of the present invention contains the above-mentioned (C) N-mono middle-chain acyl basic amino acid or a salt thereof in a proportion of generally 0.1 wt % to 7 wt %, preferably 0.5 wt % to 5 wt %, more preferably 1 wt % to 3 wt %, relative to the total amount of the composition.

The composition of the present invention contains water as component (D). In the present invention, water only needs to be suitable for the production of skin, hair or cleansing composition, and purified water such as deionized water, distilled water and the like is preferably used.

Furthermore, the composition of the present invention may contain (E) N-mono long-chain acyl basic amino acid or a salt thereof.

Further addition of (E) component can impart the composition of the present invention with superior texture after use as well as superior texture during use.

The N-mono long-chain acyl basic amino acid possibly contained as (E) component in the composition of the present invention is a basic amino acid having one long-chain acyl group bonded to the α-position amino group or ω-position amino group.

Examples of the basic amino acid constituting the N-mono long-chain acyl basic amino acid include lysine, ornithine, 2,4-diaminobutyric acid, arginine, histidine and the like.

For the object of imparting superior texture after use to the composition of the present invention, lysine is preferably used as the above-mentioned basic amino acid.

As the basic amino acid, any of L-form, DL-form and D-form may also be used, L-form and DL-form are preferably used and L-form is more preferably used.

The long-chain acyl group to be bonded to the above-mentioned basic amino acid is a saturated or unsaturated aliphatic acyl group having 12 to 24 carbon atoms, and may be linear or may have a branched chain. Specifically, dodecanoyl (lauroyl), tetradecanoyl (myristoyl), pentadecanoyl, hexadecanoyl (palmitoyl), 9-hexadecenoyl (palmitoleoyl), octadecanoyl (stearoyl), 16-methyl-heptadecanoyl (isostearoyl), cis-9-octadecenoyl(oleoyl), eicosanoyl (arachidoyl), docosanoyl (behenoyl) and the like can be mentioned.

For the object of imparting superior texture after use to the composition of the present invention, an acyl group having 12 to 18 carbon atoms is preferable, and dodecanoyl (lauroyl) is particularly preferable.

The binding site of the above-mentioned long-chain acyl group to the basic amino acid is the α-position amino group or ω-position amino group. For arginine and histidine, it is α-position amino group.

Therefore, examples of the N-mono long-chain acyl basic amino acid contained as component (E) in the composition of the present invention include $N^\varepsilon$-lauroyllysine, $N^\varepsilon$-myristoyllysine, $N^\varepsilon$-palmitoyllysine, $N^\varepsilon$-stearoyllysine, $N^\varepsilon$-isostearoyllysine, $N^\varepsilon$-oleoyllysine, $N^\varepsilon$-behenoyllysine, $N^\alpha$-lauroyllysine, $N^\alpha$-myristoyllysine, $N^\alpha$-palmitoyllysine, $N^\alpha$-stearoyllysine, $N^\alpha$-isostearoyllysine, $N^\alpha$-oleoyllysine, $N^\alpha$-behenoyllysine, $N^\delta$-lauroylornithine, $N^\delta$-palmitoylornithine, $N^\delta$-stearoylornithine, $N^\delta$-isostearoylornithine, $N^\alpha$-lauroylornithine, $N^\alpha$-palmitoylornithine, $N^\alpha$-stearoylornithine, $N^\alpha$-isostearoylornithine, $N^\gamma$-lauroyl-2,4-diaminobutyric acid, $N^\gamma$-palmitoyl-2,4-diaminobutyric acid, $N^\alpha$-lauroyl-2,4-diaminobutyric acid, $N^\alpha$-palmitoyl-2,4-diaminobutyric acid, $N^\alpha$-lauroylarginine, $N^\alpha$-palmitoylarginine, $N^\alpha$-isostearoylarginine, $N^\alpha$-lauroylhistidine, $N^\alpha$-palmitoylhistidine, $N^\alpha$-isostearoylhistidine and the like.

The N-mono long-chain acyl basic amino acid contained as component (E) in the composition of the present invention may be a free form or a salt form.

Examples of the salt of N-mono long-chain acyl basic amino acid include alkali metal salts such as sodium salt, potassium salt and the like; alkaline earth metal salts such as magnesium salt, calcium salt and the like; inorganic acid salts such as hydrochloride, nitrate salt, sulfate, carbonate and the like; organic acid salts such as acetate, lactate, citrate and the like; amino acid salts such as glutamate, aspartate and the like, and the like. From the aspects of easy availability and handleability, sodium salt, potassium salt, acetate and the like are preferable.

For the object of imparting superior texture after use to the composition of the present invention, a free form is most preferably used.

One kind of the above-mentioned N-mono long-chain acyl basic amino acid or a salt thereof may be selected and used alone, or two or more kinds thereof may be selected and used in combination From the aspect of stability of preparation formulation in the present invention, $N^\varepsilon$-lauroyllysine, particularly $N^\varepsilon$-lauroyl-L-lysine, is preferably used.

In another embodiment, (E) the N-mono long-chain acyl basic amino acid is one in which the long-chain acyl is a saturated or unsaturated aliphatic acyl group having 12 to 22 carbon atoms, excluding N-mono long-chain acyl arginine, or a salt thereof.

The above-mentioned (E) N-mono long-chain acyl basic amino acid may be, for both a free form and a salt form thereof, used by preparing according to a known production method such as the Schotten-Baumann reaction and the like in which the α position or ω position amino group is protected in advance and fatty acid chloride is added dropped as described in, for example, JP-A-60-67406, which is incorporated herein by reference in its entirety. In addition, a commercially available product such as "AMIHOPE LL" (manufactured by Ajinomoto Co., Inc.) and the like may also be used.

The composition of the present invention contains the above-mentioned (E) N-mono long-chain acyl basic amino acid or a salt thereof in a proportion of generally 0.1 wt % to 7 wt %, preferably 0.5 wt % to 5 wt %, more preferably 1 wt % to 3 wt %, relative to the total amount of the composition.

The composition of the present invention can contain other starting materials and additives generally contained in skin, hair or cleansing compositions such as other surfactant, oily starting material for cosmetics (vegetable oil, wax, hydrocarbon oil, ester etc.), moisturizer, chelating agent, thickener, anti-inflammatory agent, emollient agent, conditioning agent, texture improving agent, preservative, antioxidant, opaquer, pH adjuster, plant extract, vitamin, ultraviolet absorber, UV scattering agent, flavor, pigment, dye, coloring matter and the like besides (A) at least one kind selected from the group consisting of N-acyl acidic amino acid and a salt thereof, and N-acyl neutral amino acid and a salt thereof, (B) polyhydric alcohol, (C) N-mono middle-chain acyl basic amino acid or a salt thereof, and (D) water, or further (E) N-mono long-chain acyl basic amino acid, as long as the features of the present invention are not impaired.

Examples of other surfactants include non-ionic surfactants such as fatty acid polyglyceryl, fatty acid glyceryl, fatty acid polyoxyethyleneglyceryl, fatty acid sorbitan, fatty acid sorbitan polyoxyethylene, fatty acid polyethylene glycol, polyoxyethylene alkyl ether, fatty acid monoethanolamide, fatty acid diethanolamide, alkylglucoside and the like; anionic surfactants other than component (A) such as alkylsulfate, polyoxyethylene alkyl ether sulfate, fatty acid salt, alkylsulfonate, dialkylsulfosuccinate, alkylphosphate and the like; cation surfactants such as dialkyldimethylammonium salt, alkyltrimethylammonium salt, benzalkonium salt, trimethylammoniohydroxypropylhydroxyethylcellulose chloride, ethyl N-cocoyl-L-argininate-DL-pyrrolidone carboxylic acid salt and the like; amphoteric surfactants such as alkyldimethylaminoacetic acid betaine, fatty acid amidepropylbetaine, alkyldimethylamineoxide, 2-alkyl-N-carboxymethyl-N-hydroxyethylimidazolinium betaine, N-acyl-N'-carboxymethyl-N'-hydroxyethyl ethylenediamine salt and the like, and the like.

Examples of the oily starting material for cosmetics include vegetable oils such as almond oil, avocado oil, olive oil, macadamia nut oil, hydrogenation castor oil, hydrogenation coconut oil and the like; wax such as candelilla wax, jojoba oil, beeswax, lanolin and the like; phospholipids such as lecithin, lysophosphatidylcholine and the like; hydrocarbon oils such as light liquid paraffin, squalane, petrolatum and the like; aliphatic alcohols such as cetanol, stearylalcohol, behenyl alcohol and the like; fatty acids such as lauric acid, stearic acid and the like; esters such as diisopropyl sebacate, glyceryl caprylate, tri(caprylic acid/capric acid) glyceryl, isopropyl myristate, octyldodecyl myristate, isopropyl palmitate, diisostearyl lauroylglutamate, N-myristoyl-N-methyl-β-alanine(phytosteryl/decyltetradecyl), N-lauroyl-L-glutamic acid di(phytosteryl/octyldodecyl), N-lauroyl-L-glutamic acid di(cholesteryl/behenyl/octyldodecyl) and the like, and the like.

Examples of the moisturizer include mucopolysaccharides such as sodium hyaluronate, chondroitin sulfate and the like; amino acids and derivatives thereof such as serine, methylserine, proline, trimethylglycine, sodium glutamate, pyrrolidonecarboxylic acid, sodium pyrrolidonecarboxylate, sodium polyaspartate and the like; yeast extract and the like.

Examples of the chelating agent include sodium aluminum silicate, ethylenediaminetetraacetic acid, sodium citrate and the like.

Examples of the thickener include polysaccharides and derivatives thereof such as carrageenan, sodium carboxymethylcellulose, xanthan gum, guar gum, cornstarch, hydroxyethylcellulose, hydroxypropylmethylcellulose and the like; water-soluble polymers such as carboxyvinyl polymer, sodium polyacrylate, polyvinylpyrrolidone and the like, inorganic salts such as sodium chloride, potassium chloride and the like, and the like.

Examples of the anti-inflammatory agent include allantoin, guaiazulene and a derivative thereof (sodium guaiazulene sulfonate etc.), glycyrrhizic acid, dipotassium glycyrrhizate, glycyrrhetinic acid and acid derivative thereof (stearyl glycyrrhetinate etc.) and the like.

Examples of the emollient agent include esters such as cetyl ethylhexanoate, N-lauroyl-L-glutamic acid di(cholesteryl/behenyl/octyldodecyl) and the like; glycerol esters such as glyceryl diisostearate and the like; polyglycerol esters such as polyglyceryl diisostearate and the like; cyclic silicone such as octamethylcyclotetrasiloxane, decamethylcyclopentasiloxane and the like; modified silicones such as dimethiconol and the like, and the like.

Examples of the conditioning agent include arginine, arginine hydrochloride; alkylammonium salts such as cetyl trimethylammonium chloride, stearyltrimethylammonium chloride and the like; amideamines such as stearic acid dimethylaminopropylamide, stearic acid diethylaminoethylamide and the like; cationized polymers such as dimethyldiallylammonium chloride—acrylamide copolymer and the like, and the like.

Examples of the texture improving agent include amino acid derivatives such as sebacoyl bislaurylamide lysine salt and the like; soybean sprout extract and the like.

Examples of the preservative include sodium benzoate, phenoxyethanol, paraoxybenzoate (e.g., methyl paraoxybenzoate, propyl paraoxybenzoate etc.).

Examples of the antioxidant include γ-oryzanol, tannic acid, tocopherol, gallic acid, pyrogallol and the like.

Examples of the opaquer include opalizers such as styrene polymer, polyvinyl acetate and the like; pearlescent agents (pearly sheen agents) such as ethylene glycol monostearate, ethylene glycol distearate and the like, and the like.

Examples of the pH adjuster include citric acid, sodium citrate, gluconic acid, succinic acid, sodium hydroxide, potassium hydroxide and the like.

Examples of the plant extract include extracts of cube gambir, aloe, tea, sage, Thymus vulgaris, hamamelis, grape leaf and the like.

Examples of the vitamin include vitamin B group such as thiamine hydrochloride, pyridoxine hydrochloride, cyanocobalamin, nicotinamide, panthenol, folic acid, riboflavin and the like; vitamin C and derivatives thereof such as ascorbic acid, sodium ascorbate, ascorbyl phosphate sodium, ascorbic acid sulfate disodium salt and the like; vitamin E and derivatives thereof such as tocopheryl acetate, tocopherol, tocopherol nicotinate and the like; vitamin-like substances such as glucosyl hesperidin, glucosyl rutin and the like and the like.

Examples of the ultraviolet absorber include 2-ethylhexyl methoxycinnamate, 4-tert-butyl-4'-methoxydibenzoylmethane and the like.

Examples of the UV scattering agent include titanium oxide, zinc oxide, fine particles titanium oxide, fine particles zinc oxide and the like.

Examples of the flavor include peppermint oil, butylvanillyl ether, menthol and the like.

Examples of the pigment include extender pigments such as silicic acid, talc and the like, pearlescent pigments such as micatitanium, bismuth oxychloride and the like, and the like.

Examples of the dye or coloring matter include tar pigments such as yellow No. 203, orange No. 205, green No. 204 and the like, and the like.

The composition of the present invention can be prepared according to a general production method of a composition for skin, hair or cleansing agent.

For example, the above-mentioned (A) and component (B) are mixed by stirring at room temperature, component (D) is added, and the mixture is dissolved by stirring with heating under reduced pressure. To the solution obtained above is added component (C), the mixture is mixed by stirring, component (E) and other additives are added as necessary, and the mixture is dissolved or dispersed, cooled with stirring to precipitate component (A) as a crystal, and further cooled to 30° C. to give a creamy composition.

Alternatively, the above-mentioned (A) and component (B) are mixed at room temperature by stirring, component (D) is added, the mixture is dissolved by stirring with heating under reduced pressure, to the obtained solution is added other additive as necessary, the mixture is dissolved or dispersed, cooled with stirring to precipitate component (A) as a crystal, then component (C) and component (E) are added, and the mixture is mixed by stirring and further cooled to 30° C. to give a creamy composition.

Component (C) may be added in a powder state. To uniformly mix and dissolve in the composition, it is preferable to dissolve the component in water in advance together with a base such as sodium hydroxide and the like, and add as an aqueous solution.

Component (E) may be added in a powder state. It is preferable to dissolve the component in a basic aqueous solution and then add same.

The composition of the present invention has a good creamy appearance with high grade pearly gloss, shows good temperature stability and is superior in form stability, and also superior in the sense of use such as elongation, water miscibility and the like.

The term "form stability" here means that syneresis of composition or increase of hardness thereof is not observed not only under conditions at 25° C. but also at a high temperature (50° C.) or at a low temperature (5° C.), and a soft creamy state is maintained.

Therefore, the creamy composition of the present invention is useful as a creamy skin composition or hair composition, and can be used as it is to give skin cosmetics such as milky lotion, cream and the like, sunscreen cosmetics such as sunscreen milky lotion, sunscreen cream and the like, body cosmetics such as body toner, body cream and the like, make-up cosmetics such as liquid foundation, cream foundation and the like, hair cosmetic such as hair cream, hair conditioner and the like, and the like or by adding, where necessary, a solvent such as water, lower alcohol such as ethanol and the like, and the like, and the above-mentioned other various additives.

The content of each of the components (A), (B), (C), (E) in the above-mentioned skin cosmetics and the like is appropriately determined according to the dosage form, use object and the like. Generally, it is 0.1 wt % to 40 wt % for component (A), 1 wt % to 45 wt % for component (B), 0.05 wt % to 6.5 wt % for component (C), and 0.05 wt % to 6.5 wt % for component (E).

The creamy cleansing composition of the present invention can be used as it is to give a creamy cleansing agent or by adding, where necessary, a solvent such as water, lower alcohol such as ethanol and the like, and the like, and the above-mentioned other various additives.

The creamy cleansing agent of the present invention is superior in the appearance, form stability and sense of use, and suitable for washing skin or hair.

The content of each of the components (A), (B), (C), (E) in the creamy cleansing agent of the present invention is appropriately determined according to the dosage form, use object and the like. Generally, it is 0.05 wt % to 38 wt % for component (A), 0.5 wt % to 40 wt % for component (B), 0.03 wt % to 6 wt % for component (C), and 0.03 wt % to 6 wt % for component (E).

Therefore, the creamy cleansing agent of the present invention can be preferably provided as a skin cleanser such as facial cleanser and the like, a hair cleanser such as shampoo and the like, a body cleanser such as hand soap, body soap and the like, and the like.

Other features of the invention will become apparent in the course of the following descriptions of exemplary embodiments which are given for illustration of the invention and are not intended to be limiting thereof.

EXAMPLES

Examples 1 and 2. Creamy Cleansing Composition

According to the formulations shown in Table 1, creamy cleansing compositions were prepared according to the following production method.

Each component in Table 1 is as follows.

(i) (A) N-cocoylglycine sodium salt: "AMILITE GCS-11 (F)" (manufactured by Ajinomoto Co., Inc.) was used.

(ii) (B) glycerol: "concentrated glycerol for cosmetic" (manufactured by Kao Corporation) was used.

(iii) (C) $N^\varepsilon$-octanoyl-L-lysine: n-octanoic acid (manufactured by Tokyo Chemical Industry Co., Ltd.) (93.0 g), L-lysine (manufactured by Tokyo Chemical Industry Co., Ltd.) (84.5 g) were suspended in xylene (manufactured by KANTO CHEMICAL CO., INC.) (439.2 g) at 25° C., the obtained suspension was heated to 80° C. and stirred at 80° C. for 1 hr to form an n-octane acid L-lysine salt. The temperature of the suspension was further increased, water generated by the reaction was removed from the system by boiling the system by heating under a nitrogen atmosphere, and stirring was continued for 3 hr. After cooling, the precipitated crystals were collected by filtration, and the obtained crystals were washed using 516.0 g of 50 wt % aqueous ethanol solution and dried. The obtained $N^\varepsilon$-octanoyl-L-lysine was used as a white powder (139.5 g, yield 89.0%).

(iv) (D) water: purified water was used.

Production Method:

(1) Component (A) and component (B) were mixed by stirring at room temperature.

(2) Component (D) was added, and the mixture was heated to 70° C. to 80° C. and dissolved by stirring under reduced pressure.

(3) The mixture was cooled with stirring to crystallize component (A).

(4) An aqueous solution of component (C) prepared in advance was added to the above-mentioned solution, and the mixture was mixed by stirring.

(5) The mixture was further cooled to 30° C. to give a creamy cleansing composition.

To the creamy cleansing compositions of Examples 1, 2 was added water of component (D) instead of the aqueous solution of component (C), and the mixture was similarly prepared to give the cleansing compositions of Comparative Examples 1 and 2.

Example 3. Creamy Cleansing Composition

According to the formulation shown in Table 2, creamy cleansing compositions were prepared by the following production method.

Each component in Table 2 is as follows.

(i) (A) N-lauroyl-L-glutamic acid sodium salt: "AMISOFT LS-11(F)" (manufactured by Ajinomoto Co., Inc.) was used.

(ii) (B):

1,3-butylene glycol; "1,3-BG UK" (manufactured by Daicel Corporation) was used.

dipropylene glycol; "DPG-RF" (manufactured by ADEKA CORPORATION) was used.

(iii) (C) $N^\varepsilon$-octanoyl-L-lysine: those produced similarly to those used in the above-mentioned Examples 1, 2 were used.

(iv) (D) water: purified water was used.

(v) Other surfactants:

potassium myristate; "NONSOUL MK-1" (manufactured by NOF CORPORATION) was used.

coconut oil fatty acid monoethanolamide; "AMISOL CME" (manufactured by Kawaken Fine Chemicals Co., Ltd.) was used.

(vi) inorganic powder:

talc; "MICRO ACE P-3" (manufactured by Nippon Talc Co., Ltd.) was used.

Production Method:

(1) Component (A), other surfactant, and component (B) were mixed by stirring at room temperature.

(2) Component (D) was added, and the mixture was heated to 70° C. to 80° C. and dissolved by stirring under reduced pressure.

(3) An inorganic powder was added and sufficiently dispersed.

(4) The mixture was cooled with stirring to crystallize component (A).

(5) An aqueous solution of component (C) prepared in advance was added to the above-mentioned solution, and the mixture was mixed by stirring.

(6) The mixture was further cooled to 30° C. to give a creamy cleansing composition.

To the creamy cleansing composition of Example 3 was added water of component (D) instead of the aqueous solution of component (C), and the mixture was similarly prepared to give the cleansing composition of Comparative Example 3. In addition, the cleansing composition of Comparative Example 3 containing an increased amount of an inorganic powder was used as the cleansing composition of Comparative Example 4.

Respective cleansing compositions of Examples 1 to 3 and Comparative Examples 1 to 4 were evaluated as follows for the low temperature stability and high temperature stability.

(1) Low Temperature Stability

Respective cleansing compositions of Examples and Comparative Examples were measured for the hardness at low temperature (5° C.) and room temperature (25° C.) by the following method.

Measurement Method of Hardness of Cleansing Composition

Respective cleansing compositions were filled in 50 mL vials and preserved in a thermostatic tank at 5° C. or room temperature (25° C.) for 1 week. Immediately after taking out from the thermostatic tank, a load test was performed using a FUDOH rheometer (manufactured by RHEOTECH). That is, using table speed 2 cm/min, flat plane cylindrical adapter (diameter 1.5 cm), a load value (g) after 30 sec was measured, and taken as the hardness of the creamy composition at each temperature of 5° C. or 25° C.

From the results of the above-mentioned load test, the difference in the hardness of the cleansing composition between room temperature (25° C.) and low temperature (5° C.) ((hardness at 5° C.)–(hardness at 25° C.)) (g) was calculated and evaluated according to the following evaluation criteria. The evaluation results are also shown in Tables 1, 2.

Evaluation Criteria (i) Comparative Examples 1, 2 and Examples 1, 2

⊙; difference in hardness is not less than 11 g and less than 30 g

○; difference in hardness is not less than 30 g and less than 50 g x; difference in hardness is not less than 50 g (ii) Comparative Examples 3, 4 and Example 3

⊙; difference in hardness is not less than 21 g and less than 50 g

○; difference in hardness is not less than 50 g and less than 80 g x; difference in hardness is not less than 80 g (2) High Temperature Stability Respective cleansing compositions were each filled in a 30 mL vial, preserved in a thermostatic tank at 50° C. for 1 week, cooled to room temperature, and acclimated for 1 hr. The state of each sample was visually observed and evaluated according to the following evaluation criteria. The evaluation results are also shown in Tables 1, 2.

Evaluation Criteria good (⊙); synersis is not found
slightly poor (○); small synersis is confirmed
poor (x); synersis is clearly confirmed Sensory evaluation of the appearance and sense of use of the cleansing compositions of Example 3 and Comparative Examples 3, 4 was performed by four professional panelists and evaluated based on the following evaluation criteria.

That is, three items of luxurious feeling due to pearl-like luster in appearance, elongation of cream, water miscibility were evaluated by each panelist in three stages shown below with the cleansing composition of Comparative Example 4 as the standard product. The mean of the evaluation points of 4 panelists was calculated, and less than 0 point is indicated as "x", not less than 0 and less than 0.5 point is indicated as "Δ", not less than 0.5 and less than 1 point is indicated as "○", 1 point, namely, all members of the panelists evaluated to be +1 point is indicated as "⊙".

The evaluation results are also shown in Table 2.

Evaluation Criteria (1) Luxurious Feeling Due to Pearl-Like Luster in Appearance luxurious feel is present compared to standard product; +1 point
equal to standard product; 0 point
inferior to standard product; −1 point (2) Cream Elongation good elongation compared to standard product; +1 point
equal to standard product; 0 point
inferior to standard product; −1 point (3) Water Miscibility good water miscibility compared to standard product; +1 point
equal to standard product; 0 point
inferior to standard product; −1 point

TABLE 1

| | component | Comparative Example 1 | Comparative Example 2 | Example 1 | Example 2 |
|---|---|---|---|---|---|
| (A) | N-cocoylglycine sodium salt | 35 | 40 | 35 | 40 |
| (B) | glycerol | 35 | 40 | 35 | 40 |
| (C) | aqueous $N^\varepsilon$-octanoyl-L-lysine solution (25 wt % aqueous solution)* | | | 8 | 8 |
| (D) | water | balance | balance | balance | balance |
| | total (wt %) | 100.0 | 100.0 | 100.0 | 100.0 |
| evaluation | low temperature stability (5° C., 1 week) | X | X | ○ | ⊙ |
| | high temperature stability (50° C., 1 week) | ○ | ○ | ⊙ | ⊙ |

*Prepared by mixing $N^\varepsilon$-octanoyl-L-lysine (2 g), sodium hydroxide (0.4 g), water (5.6 g) and stirring until completer dissolution of $N^\varepsilon$-octanoyl-L-lysine at ordinary temperature.

TABLE 2

| | component | Comparative Example 3 | Comparative Example 4 | Example 3 |
|---|---|---|---|---|
| (A) | N-lauroyl-L-glutamic acid sodium salt | 35 | 35 | 35 |
| other surfactant | potassium myristate | 5 | 5 | 5 |
| | coconut oil fatty acid monoethanolamide | 1 | 1 | 1 |
| (B) | 1,3-butylene glycol | 10 | 10 | 10 |
| | dipropylene glycol | 20 | 20 | 20 |
| (C) | aqueous $N^\varepsilon$-octanoyl-L-lysine solution (25 wt % aqueous solution)* | | | 8 |
| (D) | water | balance | balance | balance |
| inorganic powder | talc | 1 | 3 | 1 |
| | total (wt %) | 100 | 100 | 100 |
| evaluation | low temperature stability (5° C., 1 week) | X | X | ⊙ |
| | high temperature stability (50° C., 1 week) | X | X | ⊙ |
| | appearance (luxurious feeling due to pearl feeling) | Δ | — | ⊙ |
| | cream elongation | Δ | — | ⊙ |
| | water miscibility | Δ | — | ⊙ |

*Prepared by mixing $N^\varepsilon$-octanoyl-L-lysine (2 g), sodium hydroxide (0.4 g), water (5.6 g) and stirring until complete dissolution of $N^\varepsilon$-octanoyl-L-lysine at ordinary temperature.

As shown in Table 1, when the cleansing compositions of Comparative Examples 1 and 2 containing the above-mentioned component (A), component (B) and component (D) and not containing $N^\varepsilon$-octanoyl-L-lysine as component (C) were preserved at 5° C. for 1 week, the hardness increased remarkably, and when it was preserved at 50° C. for 1 week, slight syneresis was found.

In contrast, when the cleansing compositions of Examples 1 and 2 containing component (C) were preserved at 5° C. for 1 week, increase in the hardness was favorably suppressed. Even when they were preserved at 5° C. for 1 week, syneresis was not found, and superiority in temperature stability and form stability was shown.

As shown in Table 2, moreover, when the cleansing composition contained other surfactants (fatty acid salt and fatty acid monoethanolamide) and an inorganic powder (talc) in addition to component (A), component (B) and component (D), the compositions of Comparative Examples 3, 4 not containing component (C) showed a remarkable increase in the hardness at low temperatures and clear syneresis at high temperatures.

In contrast, the cleansing composition Example 3 containing component (C) showed good stability in both low temperatures and high temperatures.

In addition, the cleansing composition of Example 3 was evaluated to be superior in all of the appearance (luxurious feeling due to pearl feeling), elongation and water miscibility compared to the cleansing composition of Comparative Example 4.

The Examples of the creamy cleansing agent of the present invention are sequentially shown.

Example 4. Cleansing Foam

According to the formulation shown in Table 3, cleansing foam was produced. In Table 3, "AMISOFT MK-11" (manufactured by Ajinomoto Co., Inc.) was used as component (A), a component similarly produced as the component used in Examples 1 and 2 and prepared as an aqueous solution in the presence of 5 wt % sodium hydroxide in the same manner as in Examples 1 and 2 was used as component (C), and "AMINOSOAP AR-12" (manufactured by Ajinomoto Co., Inc.) was used as other surfactant. As other components, commercially available starting materials sold for cosmetics were used.

TABLE 3

| | component | content (wt %) |
|---|---|---|
| (A) | N-myristoyl-L-glutamic acid potassium salt | 20.0 |
| (B) | 1,3-butylene glycol | 28.2 |
| | polyethylene glycol 20000 | 10.0 |
| (C) | $N^\varepsilon$-octanoyl-L-lysine (25 wt % solution) | 2.0 |
| (D) | water | balance |
| other surfactant | coconut oil fatty acid L-arginine - potassium salt | 2.5 |
| oily starting material | stearic acid | 1.0 |
| | lauric acid | 0.6 |
| moisturizer | sodium glutamate | 0.5 |
| inorganic powder | talc | 0.5 |

TABLE 3-continued

| | component | content (wt %) |
|---|---|---|
| flavor | flavor | 0.2 |
| pH adjuster | citric acid | q.s. |
| | total | 100.0 |

Production Method:

(1) Component (A), other surfactant and component (B) in Table 3 were stirred at room temperature, component (D) and a moisturizer were added and the mixture was dissolved by heating and stirring under reduced pressure.

(2) The oily starting materials were mixed, the aforementioned mixture of the oily starting materials was added to the dissolution product of (1) and uniformly mixed and dispersed therein.

(3) An inorganic powder was added the dispersion product of (2) and uniformly dispersed.

(4) The composition of (3) was cooled with stirring, a flavor was added at 50° C., the mixture was further cooled to precipitate component (A) as a crystal, component (C) was added and uniformly mixed, a pH adjuster was added, and the mixture was further cooled to 30° C. to give the cleansing foam of Example 4.

Example 5. Cleansing Foam

According to the formulation shown in Table 4, cleansing foam was produced. In Table 4, "AMISOFT LS-11(F)" (manufactured by Ajinomoto Co., Inc.) was used as component (A), a component similarly produced as the component used in Examples 1 and 2 and prepared as an aqueous solution in the presence of 5 wt % sodium hydroxide in the same manner as in Examples 1 and 2 was used as component (C), "AMISAFE LL-DS-22" (10 wt % aqueous solution) (manufactured by Ajinomoto Co., Inc.) was used as a texture improving agent, and "AJIDEW NL-50" (50 wt % aqueous solution) (manufactured by Ajinomoto Co., Inc.) was used as a moisturizer. As other components, commercially available starting materials sold for cosmetics were used.

TABLE 4

| | components | content (wt %) |
|---|---|---|
| (A) | N-lauroyl-L-glutamic acid sodium salt | 30.0 |
| (B) | propylene glycol | 12.0 |
| | dipropylene glycol | 2.0 |
| | glycerol | 3.0 |
| (C) | $N^\varepsilon$-octanoyl-L-lysine (25 wt % aqueous solution) | 0.8 |
| (D) | water | balance |
| other surfactant | coconut oil fatty acid monoethanolamide | 1.0 |
| | polyethylene glycol monostearate | 5.0 |
| pearly sheen agent | ethylene glycol monostearate | 0.5 |
| oily starting material | stearic acid | 0.5 |
| moisturizer | L-pyrrolidone carboxylic acid (50 wt % aqueous solution) | 1.0 |
| texture improving agent | sebacoyl bislauryl amide lysine disodium salt (10 wt % aqueous solution) | 0.5 |
| pH adjuster | 2 wt % aqueous citric acid solution | 0.2 |
| | total | 100.0 |

Production Method:

(1) Component (A), component (B), other surfactant and a pearly sheen agent in Table 4 were stirred at room temperature, component (D) and a moisturizer were added and the mixture was dissolved by heating and stirring under reduced pressure.

(2) An oily starting material was melted by heating, added to the dissolution product of (1) and uniformly mixed.

(3) The mixture of (2) was cooled with stirring, a pH adjuster was added at 50° C., the mixture was further cooled to precipitate component (A) as a crystal.

(4) Component (C) and a texture improving agent were mixed and added to the composition of (3).

(5) The mixture was further cooled to 30° C. to give the cleansing foam of Example 5.

Example 6. Cleansing Foam

According to the formulation shown in Table 5, cleansing foam was produced. In Table 5, "AMILITE GCK-11(F)" (manufactured by Ajinomoto Co., Inc.) was used as component (A), a component similarly produced as the component used in Examples 1 and 2 and prepared as an aqueous solution in the presence of 5 wt % sodium hydroxide in the same manner as in Examples 1 and 2 was used as component (C), and "Eldew PS-203 (manufactured by Ajinomoto Co., Inc.) was used as N-lauroyl-L-glutamic acid di(phytosteryl/2-octyldodecyl). As other components, commercially available starting materials sold for cosmetics were used.

TABLE 5

| | components | content (wt %) |
|---|---|---|
| (A) | N-cocoyl-L-glycine potassium salt | 32.00 |
| (B) | 1,3-butylene glycol | 15.00 |
| | glycerol | 17.00 |
| (C) | $N^\varepsilon$-octanoyl-L-lysine (25 wt % aqueous solution) | 4.00 |
| (D) | water | balance |
| other surfactant | potassium myristate | 1.50 |
| oily starting material | behenyl alcohol | 0.50 |
| | N-lauroyl-L-glutamic acid di(phytosteryl/2-octyldodecyl) | 1.00 |
| pearly sheen agent | ethylene glycol distearate | 2.50 |
| conditioning agent | dimethyldiallylammonium chloride - acrylamide copolymer | 0.04 |
| pH adjuster | citric acid monohydrate | 2.60 |
| | total | 100.00 |

Production Method:

(1) Component (A), component (B), and other surfactant in Table 5 were stirred at room temperature, component (D) and a conditioning agent were added and the mixture was dissolved by heating and stirring under reduced pressure.

(2) An oily starting material and a pearly sheen agent were mixed and dissolved by heating, added to the dissolution product of (1) and uniformly mixed.

(3) The mixture of (2) was cooled with stirring, a pH adjuster was added at 50° C., the mixture was further cooled to precipitate component (A) as a crystal.

(4) Component (C) was added and mixed with the composition of (3).

(5) The mixture was further cooled to 30° C. to give the cleansing foam of Example 6.

Example 7. Facial Wash Cream

According to Table 6, facial wash cream was produced. In Table 6, "AMISOFT ECS-22W (30 wt %)" (manufactured by Ajinomoto Co., Inc.) was used as component (A), a component similarly produced as the component used in Examples 1 and 2 was used as component (C), and "AMIHOPE LL" (manufactured by Ajinomoto Co., Inc.) was used as component (E). As other components, commercially available starting materials sold for cosmetics were used.

TABLE 6

| | components | content (wt %) |
|---|---|---|
| (A) | N-cocoyl-L-glutamic acid sodium salt (30 wt % aqueous solution) | 20.8 |
| (B) | 1,3-propanediol | 7.0 |
| (C) | $N^\varepsilon$-octanoyl-L-lysine | 0.3 |
| (D) | water | balance |
| (E) | $N^\varepsilon$-lauroyl-L-lysine | 0.2 |
| other surfactant | coconut oil alkylbetaine (40 wt % aqueous solution) | 1.5 |
| | N-lauroyl-N'-carboxymethyl-N'-hydroxyethyl ethylenediamine sodium salt | 1.6 |
| | glyceryl caprylate | 2.5 |
| oily starting material | jojoba oil | 4.0 |
| | macadamia nut oil | 4.0 |
| thickener | guar gum | 1.5 |
| hydrophilic thickener | 10 wt % aqueous sodium chloride solution | 3.0 |
| pH adjuster | 20 wt % aqueous citric acid solution | 3.4 |
| | total | 100.0 |

Production Method:

(1) Component (A), component (B), other surfactant, a hydrophilic thickener and a pH adjuster in Table 6 were stirred at room temperature, component (D) was added and the mixture was stirred to confirm dissolution.

(2) Component (C) and component (E) were added to the dissolution product of (1) and dispersed therein.

(3) A thickener was added and mixed with oily starting materials.

(4) The mixture of (3) was added to the dispersion product of (2) and the mixture was mixed by stirring to give the facial wash cream of Example 7.

Example 8. Hair Shampoo

According to the formulation shown in Table 7, hair shampoo was produced. In Table 7, "AMISOFT CS-22 (25 wt %)" (manufactured by Ajinomoto Co., Inc.) was used as component (A), a component similarly produced as the component used in Examples 1 and 2 was used as component (C), and "AMIHOPE LL" (manufactured by Ajinomoto Co., Inc.) was used as component (E). As other components, commercially available starting materials sold for cosmetics were used.

TABLE 7

| | components | content (wt %) |
|---|---|---|
| (A) | N-cocoyl-L-glutamic acid sodium salt (25 wt % aqueous solution) | 10.00 |
| (B) | glycerol | 5.00 |
| (C) | $N^\varepsilon$-octanoyl-L-lysine | 1.50 |
| (D) | water | balance |
| (E) | $N^\varepsilon$-lauroyl-L-lysine | 0.63 |
| other surfactant | coconut oil alkylglucoside | 6.00 |
| oily starting material | glyceryl caprylate | 2.00 |

TABLE 7-continued

| components | | content (wt %) |
|---|---|---|
| hair conditioning agent | arginine | 0.30 |
| dispersing agent | decylglucoside | 0.75 |
| | laurylglucoside | 0.75 |
| thickener | xanthan gum | 1.00 |
| neutralizer | sodium hydroxide | 0.14 |
| pH adjuster | 30 wt % aqueous citric acid solution | q.s. |
| | total | 100.00 |

Production Method:

(1) Component (A), component (B), other surfactant, an oily starting material, a hair conditioning agent and a thickener in Table 7 were stirred at room temperature, a part of component (D) was added and the mixture was dissolved by heating and stirring under reduced pressure.

(2) Component (C) and component (E) were added together with a neutralizer to the rest of component (D) and dissolved therein.

(3) To the aqueous solution of (2) was added a dispersing agent and a part of pH adjuster, and the mixture was stirred until it became uniform.

(4) The aqueous solution of (3) was added to the aqueous solution of (1), and the mixture was stirred until it became uniform.

(5) The rest of the pH adjuster was added to the aqueous solution of (4) to give the hair shampoo of Example 8.

Example 9. Body Shampoo

According to the formulation shown in Table 8, body shampoo was produced. In Table 8, "AMILITE GCK-12K (30 wt %)" (manufactured by Ajinomoto Co., Inc.) was used as component (A), a component similarly produced as the component used in Examples 1 and 2 and prepared as an aqueous solution in the presence of 5 wt % sodium hydroxide in the same manner as in Examples 1 and 2 was used as component (C), and "AJIDEW NL-50" (50 wt % aqueous solution) (manufactured by Ajinomoto Co., Inc.) was used as a moisturizer. As other components, commercially available starting materials sold for cosmetics were used.

TABLE 8

| | components | content (wt %) |
|---|---|---|
| (A) | N-cocoyl-L-glycine potassium salt (30 wt %) | 5.00 |
| (B) | glycerol | 5.00 |
| (C) | $N^\varepsilon$-octanoyl-L-lysine (25 wt % aqueous solution) | 8.00 |
| (D) | water | balance |
| other surfactant | lauric acid | 3.20 |
| | myristic acid | 4.80 |
| | palmitic acid | 1.60 |
| neutralizer | potassium hydroxide | 2.30 |
| other surfactant | polyoxyethylenelauryl ether sodium sulfate | 9.30 |
| | coconut oil fatty acid amide propylbetaine | 3.00 |
| pearly sheen agent | ethylene glycol distearate | 2.00 |
| moisturizer | L-pyrrolidone carboxylic acid (50 wt % aqueous solution) | 1.50 |
| thickener | hydroxypropylmethylcellulose | 0.15 |
| hydrophilic | sodium chloride | 0.20 |

TABLE 8-continued

| | components | content (wt %) |
|---|---|---|
| thickener | potassium chloride | 2.00 |
| preservative | preservative | q.s. |
| flavor | flavor | q.s. |
| pH adjuster | citric acid | q.s. |
| | total | 100.00 |

Production Method:

(1) Component (A), component (B), other surfactant, a neutralizer, a pearly sheen agent, a moisturizer, a thickener, a hydrophilic thickener and a preservative in Table 8 were stirred at room temperature, component (D) was added and the mixture was dissolved by heating and stirring under reduced pressure.

(2) The mixture of (1) was cooled with stirring, a flavor was added at 50° C., the mixture was further cooled to precipitate component (A) as a crystal.

(3) Component (C) was added to the composition of (2) and uniformly mixed.

(4) A pH adjuster was added and the mixture was further cooled to 30° C. to give the body shampoo of Example 9.

The Examples of the hair cosmetics prepared using the hair creamy composition of the present invention are shown next.

Example 10. Hair Conditioner

According to the formulation shown in Table 9, hair conditioner was produced. In Table 9, "AMISOFT HS-11P" (manufactured by Ajinomoto Co., Inc.) was used as component (A), and a component similarly produced as the component used in Examples 1 and 2 and prepared as an aqueous solution in the presence of 0.05 wt % sodium hydroxide in the same manner as in Examples 1 and 2 was used as component (C). As other components, commercially available starting materials sold for cosmetics were used.

TABLE 9

| | components | content (wt %) |
|---|---|---|
| (A) | N-stearoyl-L-glutamic acid sodium salt | 0.1 |
| (B) | glycerol | 8.0 |
| (C) | $N^\varepsilon$-octanoyl-L-lysine (25 wt % aqueous solution) | 8.0 |
| (D) | water | balance |
| (E) | $N^\varepsilon$-lauroyl-L-arginine | 0.20 |
| oil agent | jojoba oil | 2.50 |
| | tri(caprylic/capric acid)glyceryl | 2.50 |
| | N-lauroyl-L-glutamic acid di(phytosteryl/octyldodecyl) | 0.50 |
| | shea butter | 0.50 |
| | macadamia nut oil | 2.50 |
| emulsifier | polyglyceryl monomyristate | 1.10 |
| | sorbitan monostearate | 0.90 |
| emulsion stabilizer | cetanol | 6.00 |
| pH adjuster | citric acid | q.s. |
| preservative | paraoxybenzoate | 0.2 |
| | total | 100 |

Production Method:

(1) An oil agent, an emulsifier, an emulsion stabilizer, component (E) and a preservative are dissolved by stirring at 80° C.

(2) Component (A) and component (B) are added to component (D), and the mixture is dissolved by stirring at 80° C.

(3) (2) is added to (1) at 80° C. and the mixture is emulsified.

(4) (C) is added dropwise to (3) and the mixture is stirred.

(5) The mixture is cooled to 45° C. while stirring gently and a pH adjuster is added.

(6) The mixture is cooled to room temperature to give a product.

The Examples of the skin cosmetics prepared using the creamy composition of the present invention are shown next.

Example 11. Antiaging Cream

According to the formulation shown in Table 10, antiaging cream was produced. In Table 10, "AMISOFT HS-11P" (manufactured by Ajinomoto Co., Inc.) was used as component (A), and a component similarly produced as the component used in Examples 1 and 2 and prepared as an aqueous solution in the presence of 0.05 wt % sodium hydroxide in the same manner as in Examples 1 and 2 was used as component (C). As other components, commercially available starting materials sold for cosmetics were used.

TABLE 10

| | components | content (wt %) |
|---|---|---|
| (A) | N-stearoyl-L-glutamic acid sodium salt | 0.2 |
| (B) | glycerol | 10 |
| | methylpropanediol | 5 |
| (C) | N$^\varepsilon$-octanoyl-L-lysine (25 wt % aqueous solution) | 2 |
| (D) | water | balance |
| emollient agent | decamethylcyclopentasiloxane | 10 |
| | dimethiconol | 1 |
| texture improving agent | soybean sprout extract | 1 |
| moisturizer | sodium hyaluronate | 0.5 |
| skin conditioning agent | arginine hydrochloride | 0.5 |
| thickener | sodium polyacrylate | 0.2 |
| hydrophilic thickener | sodium chloride | 0.5 |
| preservative | phenoxyethanol | 0.2 |
| pH adjuster | citric acid | q.s. |
| | total | 100 |

Production Method:

(1) An emollient agent and a texture improving agent are dissolved by stirring at 80° C.

(2) Component (A), component (B), a moisturizer, a skin conditioning agent, a thickener, a hydrophilic thickener and a preservative are added to component (D), and the mixture is dissolved by stirring at 80° C.

(3) (2) is added to (1) at 80° C. and the mixture is emulsified.

(4) (C) is added dropwise to (3) and the mixture is stirred.

(5) A pH adjuster is added and the mixture is cooled to 45° C. while stirring gently.

(6) The mixture is cooled to room temperature to give a product.

Example 12. Milky Lotion

According to the formulation shown in Table 11, milky lotion was produced. In Table 11, "AMISOFT HS-11P" (manufactured by Ajinomoto Co., Inc.) was used as component (A), and a component similarly produced as the component used in Examples 1 and 2 and prepared as an aqueous solution in the presence of 0.05 wt % sodium hydroxide in the same manner as in Examples 1 and 2 was used as component (C). As other components, commercially available starting materials sold for cosmetics were used.

TABLE 11

| | components | content (wt %) |
|---|---|---|
| (A) | N-stearoyl-L-glutamic acid sodium salt | 0.2 |
| (B) | dipropylene glycol | 5.0 |
| | glycerol | 2.0 |
| | 1,3-butylene glycol | 0.5 |
| (C) | N$^\varepsilon$-octanoyl-L-lysine (25 wt % aqueous solution) | 0.5 |
| (D) | water | balance |
| oil agent | squalane | 7.0 |
| | petrolatum | 0.5 |
| | glyceryl monostearate | 1.0 |
| emollient agent | dimethylpolysiloxane | 1.0 |
| | dimethoxybenzylidenedioxoimidazolidine propionic acid ethylhexyl | 0.1 |
| | ectoine | 0.1 |
| emulsion aid | stearic acid | 0.1 |
| lipophilic vitamin | tocopherol nicotinate | 0.1 |
| thickener | xanthan gum | 0.2 |
| hydrophilic vitamin | L-ascorbic acid sulfate disodium salt | 0.1 |
| anti-inflammatory agent | dipotassium glycyrrhizinate | 0.1 |
| moisturizer | methylserine | 0.1 |
| | yeast extract | 0.1 |
| ultraviolet absorber | 2-ethylhexyl methoxycinnamate | 2.0 |
| | 4-tert-butyl-4'-methoxydibenzoylmethane | 0.7 |
| UV scattering agent | titanium oxide | 5.0 |
| pigment | silica | 0.2 |
| | talc | 0.5 |
| | mica | 0.5 |
| | bentonite | 0.2 |
| | iron oxide | 0.5 |
| preservative | phenoxyethanol | 0.2 |
| | paraoxybenzoate | 0.2 |
| pH adjuster | citric acid | q.s. |
| | total | 100 |

Production Method:

(1) An oil agent, an emollient agent, an emulsion aid, a lipophilic vitamin and an ultraviolet absorber are added to component (D), and the mixture is dissolved by stirring at 80° C.

(2) Component (A), component (B), a thickener, a hydrophilic vitamin, an anti-inflammatory agent, a moisturizer and a preservative are added to component (D), and the mixture is dissolved by stirring at 80° C.

(3) (2) is added to (1) at 80° C., the mixture is emulsified, and a UV scattering agent and a pigment are added.

(4) (C) is added dropwise to (3) and the mixture is stirred.

(5) A pH adjuster is added and the mixture is cooled to 45° C. while stirring gently.

(6) The mixture is cooled to room temperature to give a product.

Example 13. Milky Lotion

According to the formulation shown in Table 12, milky lotion was produced. In Table 12, "AMISOFT HS-11P"

(manufactured by Ajinomoto Co., Inc.) was used as component (A), and a component similarly produced as the component used in Examples 1 and 2 and prepared as an aqueous solution in the presence of 0.05 wt % sodium hydroxide in the same manner as in Examples 1 and 2 was used as component (C). As other components, commercially available starting materials sold for cosmetics were used.

TABLE 12

| | components | content (wt %) |
|---|---|---|
| (A) | N-stearoyl-L-glutamic acid sodium salt | 0.1 |
| (B) | 1,3-butylene glycol | 5.0 |
| (C) | $N^\varepsilon$-octanoyl-L-lysine (25 wt % aqueous solution) | 2.0 |
| (D) | water | balance |
| emollient agent | squalane | 8.00 |
| | cetyl ethylhexanoate | 3.00 |
| | propylene glycol stearate | 1.20 |
| | glyceryl stearate | 3.30 |
| | dimethylpolysiloxane | 0.80 |
| | N-myristoyl-N-methyl-β-alanine(phytosteryl/decyltetradecyl) | 1.00 |
| texture improving agent | sorbitan monostearate polyoxyethylene (20E.O.) | 0.50 |
| | polyethylene glycol monostearate | 1.50 |
| thickener | xanthan gum | 0.10 |
| emulsion aid | cetanol | 2.8 |
| emulsifier | stearic acid | 2.4 |
| antioxidant | tocopherol | 0.1 |
| preservative | sodium benzoate | 0.2 |
| | phenoxyethanol | 0.2 |
| pH adjuster | citric acid | q.s. |
| | total | 100 |

Production Method:

(1) An emollient agent, a texture improving agent, an emulsifier, an emulsion aid and an antioxidant are dissolved by stirring at 80° C.

(2) Component (A), component (B), a thickener and a preservative are added to component (D), and the mixture is dissolved by stirring at 80° C.

(3) (2) is added to (1) at 80° C. and the mixture is emulsified.

(4) (C) is added dropwise to (3) and the mixture is stirred.

(5) A pH adjuster is added and the mixture is cooled to 45° C. while stirring gently.

(6) The mixture is cooled to room temperature to give a product.

The Examples of the make-up cosmetics prepared using the creamy composition of the present invention are shown next.

Example 14. Liquid Foundation

According to the formulation shown in Table 13, liquid foundation was produced. In Table 13, "AMISOFT HS-11P" (manufactured by Ajinomoto Co., Inc.) was used as component (A), and a component similarly produced as the component used in Examples 1 and 2 was used as component (C). As other components, commercially available starting materials sold for cosmetics were used.

TABLE 13

| | components | content (wt %) |
|---|---|---|
| (A) | N-stearoyl-L-glutamic acid sodium salt | 0.2 |
| (B) | glycerol | 2 |
| | 1,3-butylene glycol | 3 |
| (C) | $N^\varepsilon$-octanoyl-L-lysine | 1 |
| (D) | water | balance |
| emollient agent | octamethylcyclotetrasiloxane | 17 |
| | cetyl ethylhexanoate | 6 |
| | N-lauroyl glutamate di(cholesteryl/behenyl/octyldodecyl) | 7 |
| | glyceryl diisostearate | 5 |
| | polyglyceryl diisostearate | 1.5 |
| ultraviolet absorber | 2-ethylhexyl methoxycinnamate | 2 |
| | 4-tert-butyl-4'-methoxydibenzoylmethane | 1 |
| solvent | ethanol | 7 |
| UV scattering agent | titanium oxide | 15 |
| texture improving agent | dimethylstearylbentonite | 0.5 |
| pigment | talc | 6 |
| | iron oxide | 5 |
| preservative | methyl paraoxybenzoate | 0.2 |
| | total | 100 |

Production Method:

(1) An emollient agent and an ultraviolet absorber are dissolved by stirring at 80° C.

(2) Component (A), component (B), a solvent and a preservative are added to component (D), and the mixture is dissolved by stirring at 80° C.

(3) Component (C), a UV scattering agent, a texture improving agent and a pigment are uniformly mixed.

(4) (3) is added to (1) and dispersed therein.

(5) (2) is gradually added while stirring (3000 rpm) (4) in a homomixer, and the mixture is emulsified by stirring for 8 min.

(6) The mixture is cooled to room temperature to give a product.

The Examples of the body cosmetics prepared using the creamy composition of the present invention are shown next.

Example 15. Body Toner

According to the formulation shown in Table 14, body toner was produced. In Table 14, "AMISOFT HS-11P" (manufactured by Ajinomoto Co., Inc.) was used as component (A), and a component similarly produced as the component used in Examples 1 and 2 and prepared as an aqueous solution in the presence of 0.05 wt % sodium hydroxide in the same manner as in Examples 1 and 2 was used as component (C). As other components, commercially available starting materials sold for cosmetics were used.

TABLE 14

| | components | content (wt %) |
|---|---|---|
| (A) | N-stearoyl-L-glutamic acid sodium salt | 0.2 |
| (B) | glycerol | 3 |
| | dipropylene glycol | 6 |
| (C) | $N^\varepsilon$-octanoyl-L-lysine (25 wt % aqueous solution) | 1 |

TABLE 14-continued

| components | | content (wt %) |
|---|---|---|
| (D) | water | balance |
| skin conditioning agent | arginine | 0.2 |
| moisturizer | trimethylglycine | 0.5 |
| solvent | ethanol | 3 |
| cation surfactant | ethyl N-cocoyl-L-argininate-DL-pyrrolidone carboxylic acid salt | 0.05 |
| texture improving agent | acrylic acid-methacrylic acid alkyl copolymer | 0.2 |
| | polyoxyethylenecholestanol ether | 0.05 |
| oily texture improving agent | egg-yolk lysophosphatidylcholine | 0.1 |
| | isostearic acid polyoxyethylene hydrogenated castor oil | 0.05 |
| chelating agent | hydroxyethyl ethylenediamine triacetic acid trisodium solution | 0.05 |
| preservative | phenoxyethanol | 0.2 |
| pH adjuster | citric acid | q.s. |
| | total | 100 |

Production Method:

(1) Component (B), a cation surfactant and an oily texture improving agent are added to a part of component (D), and the mixture is dissolved by heating and cooled to room temperature.

(2) Component (A) and a texture improving agent are added to a part of component (D), and the mixture is dissolved by stirring.

(3) A skin conditioning agent and a moisturizer are dissolved in a part of component (D), and added to (2) under reduced pressure for neutralization.

(4) A solvent, a chelating agent and a preservative are mixed with the rest of component (D) and dissolved therein. The solution is added to the components of (3), and the mixture is mixed by stirring at room temperature under reduced pressure.

(5) (1) is added to the component of (4), and the mixture is mixed by stirring at room temperature under reduced pressure.

(6) (C) is added dropwise to (5) and the mixture is stirred.

(7) A pH adjuster is added and the mixture is cooled to room temperature to give a product.

INDUSTRIAL APPLICABILITY

As described in detail above, the present invention can provide a creamy composition and a creamy cleansing composition having a creamy state with high grade pearly gloss, show good temperature stability and are superior in form stability, and also superior in the sense of use such as elongation, water miscibility and the like.

The creamy composition of the present invention is useful as a skin composition or a hair composition and favorably used for creamy skin cosmetics, sunscreen cosmetics, body cosmetics, make-up cosmetics, hair cosmetics and the like.

In addition, the creamy cleansing composition of the present invention is preferably used as a creamy cleansing agent, and can be preferably provided as a skin cleanser such as facial cleanser or the like, hair cleanser such as shampoo or the like, body cleanser such as hand soap, body soap or the like, or the like.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A creamy composition, comprising:
   (A) at least one component selected from the group consisting of an N-acyl acidic amino acid, a salt of an N-acyl acidic amino acid, an N-acyl neutral amino acid, and a salt of an N-acyl neutral amino acid;
   (B) at least one polyhydric alcohol;
   (C) at least one N-mono middle-chain acyl basic amino acid or a salt thereof; and
   (D) water,
   wherein said N-mono middle-chain acyl basic amino acid has an acyl group having 6 to 10 carbon atoms, and the content of each of the components (A), (B), (C) in the creamy composition is 0.1 wt % to 40 wt %, 1 wt % to 45 wt %, and 0.05 wt % to 6.5 wt %, respectively.

2. A creamy cleansing composition, comprising:
   (A) at least one component selected from the group consisting of an N-acyl acidic amino acid, a salt of an N-acyl acidic amino acid, an N-acyl neutral amino acid, and a salt of an N-acyl neutral amino acid;
   (B) at least one polyhydric alcohol;
   (C) at least one N-mono middle-chain acyl basic amino acid or a salt thereof; and
   (D) water,
   wherein said N-mono middle-chain acyl basic amino acid has an acyl group having 6 to 10 carbon atoms, and the content of each of the components (A), (B), (C) in the creamy cleansing composition is 0.05 wt % to 38 wt %, 0.5 wt % to 40 wt %, and 0.03 wt % to 6 wt %, respectively.

3. The composition according to claim 1, which comprises at least one N-acylglutamic acid or a salt thereof.

4. The composition according to claim 1, which comprises at least one N-acylglycine or a salt thereof.

5. The composition according to claim 1, wherein said (B) at least one polyhydric alcohol is at least one member selected from the group consisting of an alkanediol having 3 to 4 carbon atoms, glycerol, and dipropylene glycol.

6. The composition according to claim 1, wherein said (C) at least one N-mono middle-chain acyl basic amino acid or a salt thereof is $N^\varepsilon$-octanoyl lysine or a salt thereof.

7. The composition according to claim 1, further comprising:
   (E) at least one N-mono long-chain acyl basic amino acid or a salt thereof,
   wherein said N-mono long-chain acyl basic amino acid has an acyl group having 12 to 22 carbon atoms.

8. The composition according to claim 7, wherein said (E) at least one N-mono long-chain acyl basic amino acid or a salt thereof is N-lauroyllysine or a salt thereof.

9. The composition according to claim 2, which comprises at least one N-acylglutamic acid or a salt thereof.

10. The composition according to claim 2, which comprises at least one N-acylglycine or a salt thereof.

11. The composition according to claim 2, wherein said (B) at least one polyhydric alcohol is at least one member selected from the group consisting of an alkanediol having 3 to 4 carbon atoms, glycerol, and dipropylene glycol.

12. The composition according to claim 2, wherein said (C) at least one N-mono middle-chain acyl basic amino acid or a salt thereof is NE-octanoyl lysine or a salt thereof.

13. The composition according to claim 2, further comprising:
(E) at least one N-mono long-chain acyl basic amino acid or a salt thereof,
wherein said N-mono long-chain acyl basic amino acid has an acyl group having 12 to 22 carbon atoms.

14. The composition according to claim 13, wherein said (E) at least one N-mono long-chain acyl basic amino acid or a salt thereof is N-lauroyllysine or a salt thereof.

15. A cleansing agent, comprising a composition according to claim 2.

16. A method for treating skin, comprising applying a composition according to claim 1 to skin.

17. A method for cleansing skin or hair, comprising applying a composition according to claim 2 to skin or hair.

* * * * *